(12) United States Patent
Glaser et al.

(10) Patent No.: US 10,101,192 B2
(45) Date of Patent: Oct. 16, 2018

(54) RADIOMETRIC MEASURING ARRANGEMENT AND METHOD FOR DETECTION OF ACCRETION FORMATION IN A RADIOMETRIC MEASURING ARRANGEMENT

(71) Applicant: Endress + Hauser GmbH + Co. KG, Maulburg (DE)

(72) Inventors: Dirk Glaser, Steinen (DE); Martin Urban, Lorrach (DE)

(73) Assignee: ENDRESS+HAUSER SE+CO.KG, Maulburg (DE)

( * ) Notice: Subject to any disclaimer, the term of this patent is extended or adjusted under 35 U.S.C. 154(b) by 601 days.

(21) Appl. No.: 14/412,062

(22) PCT Filed: Jun. 7, 2013

(86) PCT No.: PCT/EP2013/061803
§ 371 (c)(1),
(2) Date: Dec. 30, 2014

(87) PCT Pub. No.: WO2014/005794
PCT Pub. Date: Jan. 9, 2014

(65) Prior Publication Data
US 2015/0338262 A1    Nov. 26, 2015

(30) Foreign Application Priority Data

Jul. 3, 2012   (DE) .................. 10 2012 105 922

(51) Int. Cl.
*G01N 23/10*   (2018.01)
*G01N 23/18*   (2018.01)
(Continued)

(52) U.S. Cl.
CPC ........ *G01F 23/2885* (2013.01); *G01F 23/288* (2013.01); *G01F 23/2845* (2013.01);
(Continued)

(58) Field of Classification Search
CPC ........ G01N 23/00; G01N 23/02; G01N 23/06; G01N 23/08; G01N 23/083; G01N 23/10;
(Continued)

(56) References Cited

U.S. PATENT DOCUMENTS 3,594,575 A    7/1971  Shoemaker
4,228,353 A *  10/1980 Johnson .................... G01F 1/74
                                                        250/356.1
(Continued)

FOREIGN PATENT DOCUMENTS

CN    1438475 A    8/2003
CN    1873384 A    12/2006
(Continued)

OTHER PUBLICATIONS

German Search Repport, German PTO, Munich, dated Mar. 13, 2013.
(Continued)

*Primary Examiner* — Anastasia Midkiff
(74) *Attorney, Agent, or Firm* — Bacon & Thomas, PLLC

(57) ABSTRACT

Radiometric measuring arrangement for measuring and/or monitoring a measured variable, especially a fill level or a density, of a fill substance located in a container and a method executable therewith for detection of accretion formation in the container. The variable to be measured is measured by means of a measuring system, which during operation sends radioactive radiation along a measuring path through the container, and measures radiation intensity emerging from the container along the measuring path, and by means of a comparison measuring system, which sends radioactive radiation along a comparison path through the container and measures radiation intensity emerging from the container along the comparison path. The comparison path extends in such a manner through the container that in
(Continued)

the case of the presence of an accretion layer on the inner walls of the container a ratio of a sum of the two segments of the measuring path extending through the accretion layer to the length of an additional segment of the measuring path (A, A') extending between these two segments is different from the ratio formed in the same manner for the comparison path, and an accretion formation occurring in ongoing operation is detected based on deviations ascertained in ongoing operation between the measurement results of the measuring system and the measurement results of the comparison measuring system.

9 Claims, 2 Drawing Sheets

(51) Int. Cl.
| | | |
|---|---|---|
| *G01F 23/28* | (2006.01) | |
| *G01F 25/00* | (2006.01) | |
| *G01F 23/288* | (2006.01) | |
| *G01F 23/284* | (2006.01) | |
| *G01N 9/24* | (2006.01) | |
| *G01N 23/083* | (2018.01) | |

(52) U.S. Cl.
CPC ............. *G01N 23/10* (2013.01); *G01N 23/18* (2013.01); *G01F 25/0092* (2013.01); *G01N 9/24* (2013.01); *G01N 23/083* (2013.01); *G01N 2223/302* (2013.01); *G01N 2223/3037* (2013.01); *G01N 2223/639* (2013.01)

(58) Field of Classification Search
CPC .... G01N 23/12; G01N 23/18; G01N 2223/00; G01N 2223/03; G01N 2223/04; G01N 2223/045; G01N 2223/10; G01N 2223/101; G01N 2223/1016; G01N 2223/30; G01N 2223/302; G01N 2223/303; G01N 2223/3037; G01N 2223/60; G01N 2223/628; G01N 2223/633; G01N 2223/635; G01N 2223/639; G01N 2223/645; G01N 2223/652; G01F 23/00; G01F 23/0007; G01F 23/22; G01F 23/26; G01F 23/284; G01F 23/2845; G01F 23/288; G01F 23/2885; G01F 25/00; G01F 25/0092
See application file for complete search history.

(56) References Cited

U.S. PATENT DOCUMENTS

| | | | |
|---|---|---|---|
| 4,277,681 A | | 7/1981 | Borken |
| 4,795,903 A | * | 1/1989 | Clayton ................. G01N 23/12 250/301 |
| 6,879,425 B2 | | 4/2005 | Damm |
| 7,492,859 B2 | | 2/2009 | Kulik |
| 8,878,136 B2 | | 11/2014 | Damm et al. |
| 2004/0128098 A1 | | 7/2004 | Neuhaus |
| 2006/0131496 A1 | | 6/2006 | Fitzgerald |
| 2008/0226026 A1 | | 9/2008 | Kulik |

FOREIGN PATENT DOCUMENTS

| | | |
|---|---|---|
| CN | 201163209 Y | 12/2008 |
| DE | 3037413 A1 | 4/1981 |
| DE | 102007051936 A1 | 7/2009 |
| EP | 1921435 A2 | 5/2008 |
| WO | 0218883 A2 | 3/2002 |
| WO | 2010127920 A1 | 11/2010 |

OTHER PUBLICATIONS

International Search Report, EPO, The Netherlands, dated Oct. 14, 2013.
English Translation of the International Preliminary Report on Patentability, WIPO, Geneva, dated Jan. 15, 2015.

* cited by examiner

RADIOMETRIC MEASURING ARRANGEMENT AND METHOD FOR DETECTION OF ACCRETION FORMATION IN A RADIOMETRIC MEASURING ARRANGEMENT

TECHNICAL FIELD

The invention relates to a method for detection of accretion formation in containers, in which a radiometric measuring arrangement for measuring and/or monitoring a measured variable, especially a fill level or a density of a substance located in a container, is provided, as a well as to a radiometric measuring arrangement comprising a measuring system, which during operation sends radioactive radiation along a measuring path through the container. The measuring system includes a detector, which measures radiation intensity emerging from the container along the measuring path, and an evaluation unit, which, based on calibration data of the measuring system and based on the measured radiation intensity ascertained in the case of an accretion free container, determines and outputs a measurement result corresponding to the measured variable.

BACKGROUND DISCUSSION

Radiometric measuring arrangements are applied in industrial measurements technology, for example, for measuring a fill level of a fill substance in a container, for monitoring exceeding or subceeding of a predetermined fill level of a fill substance in a container, or for measuring a density of a fill substance.

Radiometric measuring arrangements are usually applied when conventional measuring methods are not applicable due to especially rough conditions at the measuring location. Very frequently present at the measuring location are extremely high temperatures and pressures or chemically and/or mechanically very aggressive environmental influences, which make use of other measuring methods impossible.

A fundamental principle of radioactive measurements technology is that one or more radioactive radiators, such as e.g. $Co_{60}$ or $Cs_{137}$ preparations, are positioned at a measuring location in such a manner that radiation emitted by them penetrates a region to be registered metrologically, e.g. a part of a container filled with a fill substance, and a radiation intensity emerging on a container side lying opposite the radiator is measured with an appropriate detector, e.g. a scintillation detector. The emerging radiation intensity depends on the geometric arrangement and the absorption along the path traveled by the radiator to the detector. The latter is in the case of fill level measurement dependent on the fill level of the fill substance located in the measuring path in the container and in the case of density measurement on the density of the fill substance located in the measuring path. As a result, the emerging radiation intensity is a measure for the current fill level, respectively the current density, of the fill substance in the container.

There are a large number of industrial applications, in the case of which, with time, accretion can form on the inner walls of the container. The terminology, accretion, refers here to deposits of material attached to the inner walls. Accretion arises, for example, when the fill substance located in the container, or, in the case of tubular containers, flowing through the container, clings to the inner wall, and thereby establishes an accretion layer on the inner wall of the container. With time, other deposits or attached material causes the layer to become increasingly thicker.

In such case, there is the problem that the measuring path through the container leads through the layer of accreted material both in the case of its entry into the container as well as also in the case of its exit from the container. Correspondingly, both entrance side as well as also exit side, a part of the radiation sent through the container is absorbed in the accretion layer. Since the accretion layer has a higher density deviating, as a rule, from the medium, it absorbs radioactive radiation more strongly than the fill substance. In this way, the radiation intensity emerging in measurement operation is increasingly reduced, and, thus, the measurement result becomes more and more corrupted. Due to the accretion related, lower measured radiation intensity, a too high fill level, respectively a too high density, is measured. If this measurement error is not recognized, such can have fatal effects, especially in safety-relevant applications.

There is, consequently, a need to detect accretion formation in containers as early as possible. Exactly in applications in which radiometric measuring systems are applied, it is, as a rule, not, or not directly, possible to open the container, in order, in given cases, to detect accretion formation early.

Moreover, container cleaning, in the case of which accretion is removed, is, as a rule, especially complicated and expensive, particularly in these applications.

Described in U.S. Pat. No. 3,594,575 A1 is a fill level measuring arrangement, in the case of which, in given cases, accretion formation arisen in the container can be taken into consideration by a new calibration of the measuring arrangement executed on-site. In the new calibration, the dependence of the measured radiation intensities on the fill level is determined anew in the case of a currently present container state. In an ongoing operation, it is, however, not possible to detect whether accretion has formed. Insofar, as there remains even here the possibility of an unrecognized measuring result corruption due to accretion formation.

SUMMARY OF THE INVENTION

It is an object of the invention to provide a radiometric measuring arrangement and a method executable therewith, in the case of either of which accretion formation in the container of the measuring arrangement is detectable.

To this end, the invention resides in a method for accretion detection in a container, wherein a radiometric measuring system is provided for measuring and/or monitoring a measured variable, especially a fill level or a density of a fill substance located in the container, which method comprises the steps as follows:

sending during operation radioactive radiation along a measuring path through the container, measuring radiation intensity emerging from the container along the measuring path, and, based on calibration data of the measuring system and measured radiation intensity ascertained in the case of accretion free container, determining a measurement result corresponding to the measured variable; wherein, by means of a comparison measuring system, radioactive radiation is sent along a comparison path through the container, a radiation intensity emerging from the container along the comparison path is measured, and, based on calibration data of the comparison measuring system and measured radiation intensity ascertained in the case of accretion free container, a measurement result corresponding to the measured variable is determined;
  wherein the comparison path extends in such a manner through the container that, in the case of presence of an accretion layer on the inner walls of the container, a ratio of a sum of the two segments of the measuring path extending through the accretion layer to the length of an additional segment of the measuring path extending between these two segments is different from the ratio formed in the same manner for the comparison path; and
 an occurrence of accretion formation is detected based on deviations ascertained in ongoing operation between the measurement results of the measuring system and the measurement results of the comparison measuring system.

In a preferred embodiment, the ratio of the sum of the two segments of the measuring path extending through the accretion layer to the length of the additional segment of the measuring path extending between these two segments is smaller than the ratio formed in the same manner for the comparison path.

In an additional preferred embodiment, the exceeding of a predetermined threshold value for the deviation between the two measurement results means that an accretion formation in the container corrupting the radiometric measuring of the measured variable has been detected.

Moreover, preferably a need dependent scheduling of container cleanings is performed based on the deviations between the measurement results of the measuring system and the measurement results of the comparison measuring system.

Additionally, the invention resides in a further development of the method, wherein, in the case of a known density of the accretion, a thickness of the accretion layer in the container is determined based on;
  the radiation intensity measured with the measuring system and the radiation intensity measured with the comparison measuring system; and
  a container geometry and positions of measuring and comparison paths in the container.

A further development of the latter further development includes a method, in the case of which, based on the radiation intensity measured with the measuring system, the thickness and the density of the present accretion layer, a measurement result corrected as regards an accretion related measurement error is determined.

Moreover, the invention resides in a radiometric measuring arrangement for measuring and/or monitoring a measured variable, especially a fill level or a density, of a fill substance located in a container, comprising:
 a measuring system,
  which during operation sends radioactive radiation along a measuring path through the container,
  which includes a detector, which measures a radiation intensity emerging from the container along the measuring path, and
  which includes an evaluation unit, which, based on calibration data of the measuring system and the measured radiation intensity ascertained in the case of accretion free container, determines and outputs a measurement result corresponding to the measured variable; and
 a comparison measuring system,
  which during operation sends radioactive radiation along a comparison path through the container,
  wherein the comparison path extends in such a manner through the container that in the case of presence of an accretion layer on the inner walls of the container a ratio of a sum of the two segments of the measuring path extending through the accretion layer to the length of an additional segment of the measuring path extending between these two segments is different from the ratio formed in the same manner for the comparison path,
  which includes a detector, which measures a radiation intensity emerging from the container along the comparison path; and
  which includes an evaluation unit, which, based on calibration data of the comparison measuring system and the measured radiation intensity ascertained in the case of accretion free container, determines a measurement result corresponding to the measured variable and provides such for detection of accretion formation in the container, wherein accretion is detected based on deviations ascertained in ongoing operation between the measurement results of the measuring system and the measurement results of the comparison measuring system.

In a preferred embodiment, the radiometric measuring arrangement includes, connected to the measuring system and to the comparison measuring system, an evaluating unit, which during operation continuously determines deviations between the measurement results of the measuring system and the measurement results of the comparison measuring system.

A first variant of the invention includes a radiometric measuring arrangement, in the case of which the measuring system and the comparison measuring system each has a radioactive radiator arranged externally on the container, and in the case of which the detectors of the measuring system and the comparison measuring system are each arranged externally on the container on a side of the container lying opposite the respective radiator along the measuring, respectively the comparison, path.

In a preferred embodiment of the first variant, the container has a circular cross sectional area, and the measuring path extends parallel to and offset from the comparison path.

A second variant of the invention includes a radiometric measuring arrangement, in the case of which
 there is provided arranged externally on the container only a single radioactive radiator, which during operation transmits radiation along the measuring path and along the comparison path,
 the measuring path and the comparison path extend at an angle to one another,
 the detector of the measuring system is arranged externally on the container on a side of the container lying opposite the single radiator along the measuring path, and
 the detector of the comparison measuring system is arranged externally on the container on a side of the container lying opposite the single radiator along the comparison path.

Additionally, the invention resides in a variant of a radiometric measuring arrangement of the invention, in the case of which
 each of the measuring system and the comparison measuring system is a system for detecting and/or monitoring an ex- or subceeding of a predetermined fill level in the container,
 each of the measuring system and the comparison measuring system has an output, via which it outputs a measurement result corresponding to radiation intensity measured by it and based on calibration data ascertained in the case of accretion free container, and the measuring system detects and/or monitors the ex- or subceeding of the predetermined fill level based on the measured radiation intensity or based on the measurement results.

BRIEF DESCRIPTION OF THE DRAWINGS

The invention and other advantages will now be explained in greater detail based on the figures of the drawing, in which three examples of embodiments are presented; equal parts are provided in the figures with equal reference characters. The figures of the drawing show as follows.

DETAILED DISCUSSION IN CONJUNCTION WITH THE DRAWINGS

Figure 1:
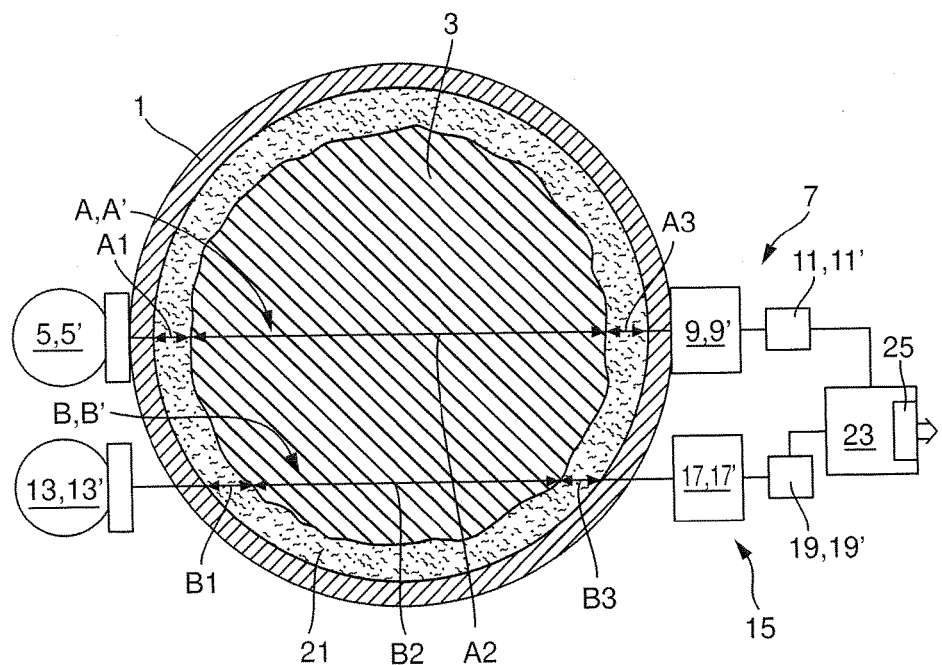
FIG. 1 is a radiometric density measuring arrangement in cross section.

FIG. 1 shows, for measuring and/or monitoring a measured variable, especially a fill level or a density $\varrho$ of a fill substance 3 located in a container 1, a sketch of the principles of a first example of an embodiment of a radiometric measuring arrangement of the invention, with which the method of the invention for detection of accretion formation in the container 1 of the measuring arrangement is performable. The invention will, first of all, be described using the example of a measuring arrangement for measuring the density $\varrho$ of the fill substance.

Container 1 is shown here in cross section and is, for example, a pipe, through which the fill substance 3 flows, or a standing, cylindrical tank, which contains the fill substance 3.

The measuring arrangement includes a measuring system, with which the density $\varrho$ of the fill substance 3 is measured. The measuring system includes, arranged externally on the container 1, a radioactive radiator 5, which during operation sends radioactive radiation along a measuring path A through the container 1. For achieving an as high as possible accuracy of measurement, the measuring path A passes preferably through a midpoint of a cross sectional area of the container 1. In this way, the part of the measuring path A relevant for the accuracy of measurement in the container 1 has in the container 1 a maximum possible length, so that the measurement effect is maximum.

Figure 2:
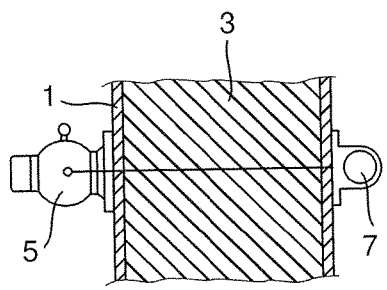
FIG. 2 is a longitudinal section through the density measuring arrangement of FIG. 1 in the plane of the measuring system.

Moreover, the measuring system includes a measuring unit 7, which measures a radiation intensity emerging from the container 1 along the measuring path A, and, based on calibration data of the measuring system and the measured radiation intensity ascertained in the case of accretion free container 1, determines and outputs a measurement result corresponding to the measured variable, here the density $\varrho$. FIG. 2 shows, in this connection, a longitudinal section through the radiometric measuring arrangement of FIG. 1 in the plane of the measuring system.

Measuring unit 7 includes, for this, a detector 9, which converts the radiation intensity striking thereon into an electrical signal reflecting the measured radiation intensity, and an evaluation unit 11 connected thereto, which, based on the electrical signal and the calibration data, determines and outputs a measurement result corresponding to the measured density $\varrho$.

The calibration data are determined in the simplest case by a two point alignment, which, for example, in the context of a start-up of the measuring system, is executed with an accretion free container 1. For this, for example, the radiation intensity is measured, which impinges on the detector 9, when such is filled with a fill substance 3, which has a density $\varrho_{min}$ corresponding to a measuring range lower limit of the measuring system, and the radiation intensity is measured, which impinges on the detector 9, when such is filled with a fill substance 3, which has a density $\varrho_{max}$ corresponding to a measuring range upper limit of the measuring system. From these two measurement points giving the radiation intensity measured as a function of the density, a scale can then be defined, based on which each radiation intensity measured in measurement operation and lying between the two extreme values is associated with a particular density $\varrho$. This is presented here, however, only as a possible example. In radiometric measurements technology, as a rule, more complex calibration methods are applied, which utilize, for example, more alignment points, linearizing methods, as well as compensation methods for compensation of dependencies of the measured radiation intensity on additional process variables, such as, for example, temperature.

According to the invention, the measuring arrangement includes, moreover, a comparison measuring system, with which the density $\varrho$ of the fill substance 3 is likewise measured. The latter can be embodied identically to the measuring system. Also this includes in the illustrated example of an embodiment, arranged externally on the container 1, a radioactive radiator 13, which during operation sends radioactive radiation along a comparison path B through the container 1, and a measuring unit 15, which measures by means of a detector 17 a radiation intensity emerging from the container 1 along the comparison path B. Detector 17 is connected with an evaluation unit 19, which, based on calibration data of the comparison measuring system and the measured radiation intensity ascertained in the case of accretion free container, determines a measurement result corresponding to the density $\varrho$.

According to the invention, the comparison path B extends in such a manner through the container 1 that in the case of presence of an accretion layer 21 on the inner walls of the container 1, a ratio VA of the path lengths extending along the measuring path A in the interior of the container 1 within and outside the accretion layer 21 is different from the corresponding ratio VB along the comparison path B. In such case, it is to be taken into consideration that the measuring path A and the comparison path B each extend input side through the accretion layer 21, which adheres internally on the container wall facing the respective radiator 5, 13, and output side through the accretion layer 21, which adheres internally on the container wall facing the respective detector 9, 17.

The ratios VA, VB are given, in each case, by the ratio of the sum of the lengths of the segments A1, A3, respectively B1, B3 of the respective radiation path extending input side and output side through the accretion layer 21 to the additional segment A2, respectively B2, of the respective radiation path extending respectively between these two segments. I.e. measuring path A and comparison path B are specified according to the invention in such a manner that:

$$VA = \frac{A1 + A3}{A2} \neq VB = \frac{B1 + B3}{B2}$$

This condition is directly fulfillable in any container 1, since the two paths are positioned and oriented in such a manner that their sections leading through the container interior have different lengths. Such is always possible for any container cross-section. Thus, for example, the measuring path A can be led in a broadest region of the container 1 through the container middle, while the comparison path B traverses only an edge region of the container 1.

In the illustrated example of a container 1 with circularly shaped cross section, this is implemented by leading measuring path A and comparison path B parallel to one another and offset from one another through the container 1, wherein the measuring path A passes through the broader container middle.

Since, from the above explanations regarding the accuracy of measurement achievable with the measuring system, preferably the path with the greatest total length extending in the container interior is used as measuring path A, the ratio VA is preferably smaller than the ratio VB. Such offers the additional advantage that the measurement result along the measuring path A, due to the smaller ratio VA, also experiences a lesser degrading of the measurement result from accretion formation.

Due to the calibration of measuring system and comparison measuring system in the case of accretion free container 1, the measurement results of the two systems agree in the case of accretion free container 1, within the achievable accuracy of measurement.

If the measuring arrangement in the case of accretion free container 1 is placed in service, the measurement results thus, first of all, agree. If there forms in ongoing operation an accretion layer 21 on the container inner walls growing with time in its thickness, then the two measurement results change as a function of the density $\varrho^A$ and the thickness of the accretion layer 21.

The reason for this is that measuring system and comparison measuring system then no longer register exclusively the desired density $\varrho$ of the fill substance 3, but, instead, an average density present along the respective radiation path in the container interior. Since the accretion layer 21 usually has a higher density $\varrho^A$ than the fill substance 3, the two measurement results increase with increasing thickness and with increasing density $\varrho^A$ of the accretion layer 21.

In such case, there holds for the average density $\varrho_{meas}$ measured by the measuring system:

$$\rho_{meas} = \frac{(A1 + A3)\rho^A + A2\rho}{A1 + A2 + A3}$$

Correspondingly, there holds for the average density $\varrho_{comp}$ determined by the comparison measuring system:

$$\rho_{comp} = \frac{(B1 + B3)\rho^A + B2\rho}{B1 + B2 + B3}$$

Due to the paths predetermined according to the invention, however, the density $\varrho_{meas}$ measured by the measuring system increases with increasing thickness and density of the accretion layer 21 significantly slower than the density $\varrho_{comp}$ measured with the comparison measuring system. This means that the measurement results of measuring system and comparison measuring system deviate increasingly from one another with increasing density $\varrho^A$ and increasing thickness of the accretion layer 21.

Correspondingly, accretion formation in the container 1 is detected according to the invention based on deviations of the measurement results of measuring system and comparison measuring system ascertained in ongoing operation. In such case, for example, the ratio of the two measurement results can be calculated as a quantitative measure of the deviation. Alternatively, also their difference can be taken into consideration as a measure.

In such case, the size of the deviation is a measure for degradation of the accuracy of measurement of the radiometric measuring arrangement. Correspondingly, a threshold value can be predetermined for the deviation, the exceeding of which threshold value means that an accretion formation in the container 1 corrupting the radiometric measurement of the measured variable has been detected. Measurement corrupting accretions can, thus, be detected early and correspondingly taken into consideration.

Moreover, the deviations between the measurement results of the measuring system and the measurement results of the comparison measuring system ascertained in ongoing operation can be used for need dependent scheduling of container cleanings. In such case, the time development of the deviations can be taken into consideration, in order to make predictions concerning the point in time when the deviation will exceed the threshold value, or some other, for example, user defined criterion making a cleaning required.

If the density $\varrho^A$ of the accretion is known, then, based on
 the radiation intensity $I_A$ measured with the measuring system
 the radiation intensity $I_B$ measured with the comparison measuring system
 the container geometry,
 the position and the length of measuring and comparison paths A, B, and
 the density $\varrho^A$ of the accretion,
a thickness d of the accretion layer 21 adhering in the container 1 can be approximately calculated.

The measured radiation intensities $I_A$, $I_B$ required for this are determined in the case of the measuring in any event, and can, thus, be directly used. Alternatively, they can be determined by back calculating based on the measurement results of the measuring system and the measurement results of the comparison measuring system and the associated calibration data.

The thickness determination offers the advantage that the measurement result $\varrho_{meas}$ of the measuring system can be corrected as regards the therein contained accretion related measurement error based on thickness d and density $\varrho^A$ of the present accretion layer 21.

Under the assumption that the thickness d of the accretion layer 21 on the container inner walls is uniform, based on the container geometry and the positions of the measuring and comparison paths A, B in the container 1, a ratio k of the sum D'=B1+B3 of the lengths of the segments extending entrance side and exit side along the comparison path B through the accretion layers 21 to the sum D=A1+A3 of the lengths of the segments extending entrance side and exit side along the measuring path A through the accretion layers 21 can be determined. I.e.:

$$k = \frac{D'}{D} = \frac{B1+B3}{A1+A3}$$

This ratio k is subsequently assumed as constant for simplifying understanding of the thickness determination method and the correction method. Actually, however, the ratio k is in most measuring arrangements dependent on the thickness d. In such case, the method steps given below are basically analogously performable. The individual equations presented below are in that case, however, no longer analytically but, instead, only numerically solvable.

In the case of an accretion layer 21 of uniform thickness d, the radiation intensity $I_A$ measured by the measuring system is:

$$I_A = I_{0A} e^{-\mu \rho^A D} e^{-\mu \rho^M (XA-D)} \quad (1)$$

wherein XA=A1+A2+A3, and
wherein other parameters are defined as follows:

$I_{0A}$ a starting intensity dependent on the radiation intensity sent by the radiator 5, the applied radiation source and the square of the distance between the radiator 5 and the detector 9, D the sum of the lengths of the segments extending input side and output side through the accretion layer 21 (D=A1+A3), $\rho^M$ the density of the medium 3, $\rho^A$ the density of the accretion layer 21, XA the known total container 1 length of the measuring path A, and μ a proportionality constant assumed here as approximately equal in the medium 1 and in the accretion layer 21 for the fill substance 3 and the accretion to show the exponential dependence of the radiation attenuation on the density of the irradiated material. The proportionality constant μ is, as a rule, at least approximately known, or can be determined by reference measurements.

Correspondingly, the radiation intensity $I_B$ measured by the comparison measuring system is:

$$I_B = I_{0B} e^{-\mu \rho^A kD} e^{-\mu \rho^M (XB-kD)} \quad (2)$$

wherein XB=B1+B2+B3, and
wherein other parameters are defined as follows:

$I_{0B}$ a starting intensity dependent on the radiation intensity sent by the radiator 13, the applied radiation source and the square of the distance between the radiator 13 and the detector 17, XB the known total length of the comparison path B in the container 1, and μ the above explained proportionality constant.

By dividing by $I_{0A}$, taking the log and solving equation (1), one obtains an expression for the density $\rho^M$ of the medium 3 as follows:

$$\rho^M = -\frac{\left(\mu \rho^A D + \ln\left(\frac{I_A}{I_{0A}}\right)\right)}{\mu (XA-D)} \quad (3)$$

If one inserts this expression into an equation obtained by division by $I_{0B}$ and subsequent taking the log of equation (2):

$$-\ln\left(\frac{I_B}{I_{0B}}\right) = \mu \rho^A kD + \mu \rho^M (XB-kD) \quad (4)$$

There results in the case of constant k a quadratic equation for D, from which D can be determined.

Under the above made assumption of a uniform thickness d of the accretion layer 21, the thickness d can now be determined based on D, the geometry of the container 1 and the position of the measuring path A in the container 1. In the example of an embodiment illustrated in FIG. 1, the two segments A1 and A3 extending along the measuring path A through the accretion layer 21 are clearly equally long, so that the thickness d of the accretion layer 21 is here determined by d=½D.

Based on the radiation intensity $I_A$ measured with the measuring system, the thickness d and the density $\rho^A$ of the accretion layer 21, there can now be determined according to equation (3) a measurement result for the density of the medium corrected relative to the accretion related measurement error.

In this way, the influence of accretion formation on the achievable measurement accuracy can clearly be reduced. Correspondingly, the time periods between following container cleanings can be optimally adapted as a function of the application dependent, required accuracy of measurement. Since cleaning occurs now only in the case of need and no longer as a matter of precaution, a lengthening of the time intervals between sequential cleanings is obtained.

In the simplest case, the accretion detection can be performed by the operator of the measuring arrangement by comparing the output, respectively displayed, measurement results of the measuring system and the comparison measuring system.

Preferably, however, this procedure is automated by equipping the radiometric measuring arrangement with an evaluation unit 23 connected with the measuring system and the comparison measuring system for continuously determining during operation the deviations between the measurement results of the measuring system and the measurement results of the comparison measuring system. For this, the evaluation unit 23 includes preferably an intelligent electronic unit, such as e.g. a microprocessor, which performs, besides the pure deviation determination, other software based functionalities, such as e.g.

comparing the deviations with the threshold value, scheduling need dependent container cleaning, determining the thickness d of the accretion layer 21 in the case of known density $\rho^A$ of the accretion, as well as in the case of known density $\rho^A$ of the accretion and therefrom ascertained thickness d of the accretion layer 21, correcting the accretion related measurement error of the measuring system.

In such case, the evaluating unit 23 must naturally also be fed the measured variables and parameters required for performing the additional functionalities, especially the measured radiation intensities $I_A$, $I_B$, the associated starting intensities $I_{0A}$, $I_{0B}$, the ratio k of the sum D'=B1+B3 of the lengths of the segments extending along the comparison path B through the accretion layers 21 to the sum D=A1+A3 of the lengths of the segments extending along the measuring path A through the accretion layers 21, and the proportionality constant μ.

The evaluating unit 23 is preferably equipped with an output system 25, via which it selectively outputs, displays and/or provides for additional evaluation and/or processing the deviations, the next cleaning date, the thickness d of the accretion layer 21, and/or the corrected measurement result of the measuring system.

Moreover, it can supplementally be equipped with an alarm, which is triggered, for example, when the deviation achieves a threshold value predetermined for such. Moreover, naturally other measurement results based, alarm initiating criteria can be created.

Figure 3:
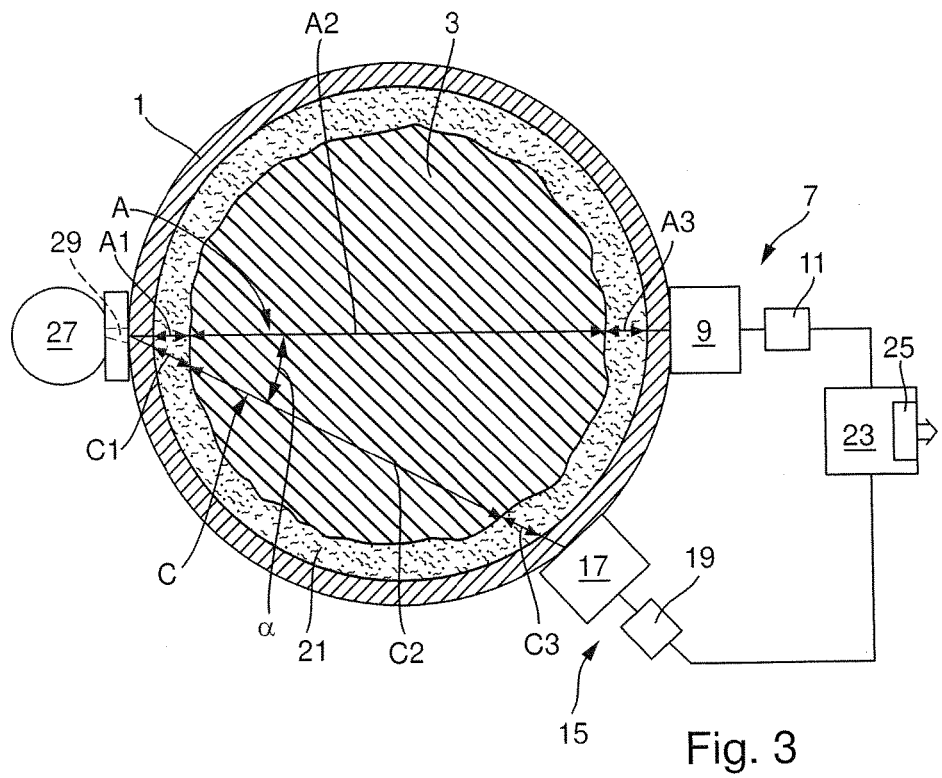
FIG. 3 is an alternative embodiment of a density measuring arrangement of the invention.

FIG. 3 shows a variation of the radiometric measuring arrangement illustrated in FIG. 1. It differs from the form of embodiment illustrated in FIG. 1 only in that it has externally arranged on the container 1 just a single radioactive radiator 27, which during operation transmits radiation along the measuring path A and on a comparison path C extending here at an angle α from the measuring path A. This is effected, for example, by applying as the single radiator 27 a point shaped radioactive source, which is placed in a radiation protection container, which has an exit opening 29 with an aperture angle corresponding to the angle α. Also, in the case of this variant, measuring path A and comparison path C are selected in such a manner that the corresponding ratios VA and VC of the sum of the lengths of the segments extending in the accretion layers A1, A3, respectively C1, C3, to the lengths of the segments A2, C2 extending therebetween in the medium 3 is different for the two paths, i.e.:

$$VA = \frac{A1 + A3}{A2} \neq VC = \frac{C1 + C3}{C2}$$

Preferably, the measuring path A also extends here again through the region of the container 1, in the case of which the total length extending within the container 1 along this measuring path A is maximum. In case required due to conditions on-site, also an orientation can be selected, in the case of which the two paths each extend at an angle to a diagonal through a container cross-section, i.e. to a diameter of the here circularly shaped container cross-section. In that case, the angles of the two paths from the diagonal must, however, be different, in order to assure the inequality of the ratios VA and VC.

The measuring system and the comparison measuring system comprise also here, again, respectively, detectors 9, 17 arranged externally on the container 1 and the thereto connected evaluation units 11, 19. Also here, the detector 9 of the measuring unit 7 of the measuring system is arranged externally on the container 1 on a side of the container 1 lying opposite the radiator 27 along the measuring path A, and the detector 17 of the measuring unit 15 of the comparison measuring system is arranged externally on the container 1 on a side of the container 1 lying opposite the single radiator 27 along the comparison path C.

Figure 4:
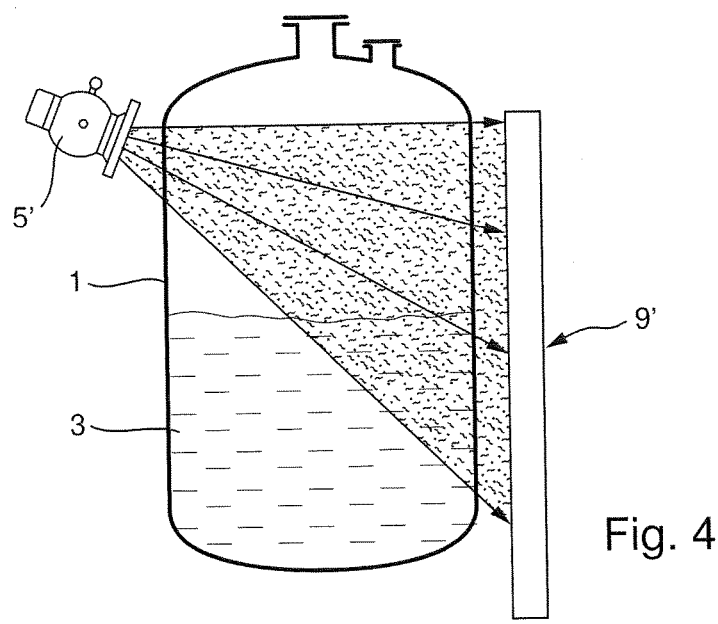
FIG. 4 is a longitudinal section through a fill level measuring arrangement in the plane of the measuring system.

The invention is also applicable in radiometric measuring arrangements for fill level measurement. Applied here according to the invention is again a measuring system for determining the fill level in the container 1 with corresponding measurement results and a corresponding comparison measuring system, with which likewise the fill level in the container 1 is measured. FIG. 4 shows a longitudinal section through such a measuring arrangement in the plane of the measuring system.

In contrast to density measurement, for fill level measurement, applied preferably externally arranged in the upper region of the container 1 are radioactive radiators 5', 13', whose radiation is transmitted collimated in the horizontal direction, however, in the vertical direction, it is transmitted with an aperture angle β. This happens regularly by placing a point shaped radiator in a radiation protection container, which has a correspondingly formed exit opening. In this way, it is achieved that the radiation in the vertical direction is sent into that region of the container 1 fixed by the aperture angle β, over which the fill level should be registered. For measuring the radiation intensity emerging in the vertical direction over this region along the radiation path, a detector 9', 17' covering this region is used, e.g. a detector equipped with a scintillation rod of appropriate length. These differences related to the measured variable concern naturally both the measuring system as well as also the comparison measuring system.

It should be pointed out that the accretion detection occurs in the same manner already described above as regards the density measuring arrangement. Applied in such case, due to the transmitted radiative power being greater in any event resulting from the vertical aperture angle β, is preferably the, as regards construction, variant corresponding to the form of embodiment illustrated in FIG. 1 with two radioactive radiators 5', 13'. In such case, for fill level measurement, the radiator 5' sends radiation along the measuring path A' collimated in the horizontal direction and fanned out in the vertical direction over the aperture angle β, and the radiator 13' sends radiation along the comparison path B' collimated in the horizontal direction and fanned out in the vertical direction over the aperture angle β.

In the case of parallel measuring and comparison paths A', B' in a container 1 with circularly shaped cross section, the picture in plan view for radiometric fill level measurement is the same as that shown in FIG. 1 for density measurement. The corresponding reference characters of the fill level measuring arrangement have therefore been given in FIG. 1 alongside the reference characters of the density measuring arrangement.

In applications, in which there are basically no concerns relative to increased radiation exposure, naturally also a form of embodiment corresponding to the variant illustrated in FIG. 3 for density measurement with only a single radiator could be applied for transmitting radiation in the horizontal direction with the aperture angle α and in the vertical direction with the aperture angle β.

Also in fill level measuring arrangements of this type, the thickness d of the accretion layer 21 can be determined approximately based on the deviations of the measurement results of measuring and comparison systems. In such case, because of the fundamental physical principle being applied, the basic explanations set forth above in conjunction with density measurement hold analogously. However, in the case of fill level measurement, a radiation intensity integrated over the height of the measuring range is measured, from which, based on calibration data determined in the case of accretion free container 1, the fill level is derived. This is taken into consideration in setting up the basic equations from the physical conditions for determining the thickness d of the accretion layer 21 and, based on the thickness d, the correction of the fill level, measurement results of the measuring system. Additionally, the absorption characteristics of the fill substance 3 are taken into consideration. Fill level measuring systems are regularly designed as regards the sent radiative power in such a manner that their radioactive radiation is completely absorbed in the fill substance 3. In that case, only the irradiated region of the container 1 located above the surface of the fill substance contributes to the deviation between the measurement results of measuring system and comparison system. There are, however, also measuring systems, in the case of which higher radiation powers are applied, so that some radiation passes through the fill substance 3. In that case, the entire height of the measuring range and the absorption in the fill substance 3 are taken into consideration. In such case, the absorption in the fill substance 3 must be known or ascertained. It is determinable, for example, based on the density $\varrho^M$ of the fill substance 3, which is usually assumed as known in fill level measuring applications. Fundamentally, the accretion detection of the invention is also applicable in connection with radiometric measuring arrangements, which determine and/or monitor an ex- or subceeding of a predetermined fill level. In such case, an ex- or subceeding of this predetermined fill level is registered with a radiometric measuring system arranged at the height of a predetermined fill level. These measuring arrangements, frequently referred to as limit switches, differ from density measuring systems essentially only by the further processing of the measured radiation intensity. Also in the case of limit switches, using an accretion free container 1, a two point calibration is performed at a fill level lying below and at a fill level lying above the predetermined fill level to be monitored. Also here, the two radiation intensities measured in the case of the two point calibration in the accretion free container 1 define a scale, based on which measurement results can be derived from intensities measured during operation.

The accretion detection can, thus, also be performed here based on these measurement results in the manner already described above in connection with the density measuring arrangement. In such case, the above details already explained above in connection with the density measuring system hold equally for the construction and positioning of the measuring system and the comparison measuring system, as well as for the measuring path and the comparison path.

For detecting and/or monitoring the ex- or subceeding of the predetermined fill level, it suffices to establish, based on the radiation intensities measured in the case of the two point calibration, a threshold value for the measured radiation intensity or for the measurement result derived therefrom based on the calibration data. Upon exceeding this threshold value, a subceeding of the predetermined fill level is displayed and, conversely. Accretion detection cannot, however, be performed based on this detecting, respectively monitoring.

In order to be able to perform the accretion detection in the above described manner, the measuring system embodied as a limit switch and the comparison measuring system embodied as a limit switch must be connected with an output, via which the above described measurement result of the respective system for accretion detection is available as determined based on the calibration data in the case of accretion free container.

The invention claimed is:

1. A method for accretion detection in a tubular container, in which a radiometric measuring system is provided for measuring a measured variable,
    wherein said measured variable is a fill level or a density of a fill substance located in said container, and
    wherein accretion occurs in the form of an accretion layer deposited on the inner walls of said container, comprising steps as follows:
    by means of said measuring system sending gamma ray radiation along a measuring path through the container, measuring gamma ray radiation intensity emerging from the container along the measuring path, and, based on calibration data of the measuring system ascertained in case of accretion free container and said measured gamma ray radiation intensity, determining a measurement result corresponding to the measured variable;
    by means of a comparison measuring system, sending gamma ray radiation along a comparison path through the container, measuring a comparison gamma ray radiation intensity emerging from the container along the comparison path, and, based on calibration data of the comparison measuring system ascertained in case of accretion free container and said measured comparison gamma ray radiation intensity, determining a comparison measurement result corresponding to the measured variable, wherein the comparison path extends in such a manner through the container that, in the case of the presence of said accretion layer on the inner walls of the container, a ratio of a sum of the lengths of two accretion segments of the comparison measuring path, said two accretion segments extending through the accretion layer, to the length of an additional segment of the comparison measuring path extending between these two accretion segments is different from a ratio of the sum of the lengths of the two accretion segments of the measuring path extending through the accretion layer, to the length of an additional segment of the measuring path extending between the two accretion segments of the measuring path;
    determining a deviation between the measurement results of the measuring system and the comparison measurement results of the comparison measuring system; and
    detecting accretion based on said deviation.

2. The method as claimed in claim 1, wherein:
    the ratio of the sum of the lengths of the two accretion segments of the measuring path extending through the accretion layer to the length of the additional segment of the measuring path extending between the two accretion segments of the measuring path is smaller than the ratio of the sum of the lengths of the two accretion segments of the comparison measuring path, to the length of the additional segment of the comparison measuring path extending between the two accretion segments of the comparison measuring path.

3. The method as claimed in claim 1, wherein:
    a need dependent scheduling of container cleanings is performed based on deviations between the measurement results of the measuring system and the comparison measurement results of the comparison measuring system.

4. The method as claimed in claim 1, wherein:
    in the case that the density of the accretion material is known, a thickness of the accretion layer in the container is determined based on
    the gamma ray radiation intensity measured with the measuring system,
    the comparison gamma ray radiation intensity measured with the comparison measuring system,
    a container geometry, and
    positions of the measuring path and comparison paths in the container.

5. The method as claimed in claim 4, wherein:
    based on the gamma ray radiation intensity measured with the measuring system, and based on the thickness and the density of the present accretion layer, a corrected measurement result is determined with regard to an accretion related measurement error of the measured gamma ray radiation intensity.

6. A radiometric measuring arrangement for measuring a measured variable, of a fill substance located in a tubular container, and for detecting accretion, wherein said measured variable is a fill level or a density of said fill substance located in said container, and wherein accretion occurs in form of an accretion layer depositing on the inner walls of said container, comprising:
a measuring system;
wherein said measuring system sends gamma ray radiation along a measuring path through the container, said measuring system including a detector, wherein said detector measures a gamma ray radiation intensity emerging from the container along the measuring path, and
said measuring system including an evaluation unit, wherein said evaluation unit, based on calibration data of the measuring system ascertained in case of the accretion free container and the measured gamma ray radiation intensity, determines and outputs a measurement result corresponding to the measured variable; and
a comparison measuring system;
said comparison measuring system sending gamma ray radiation along a comparison path through the container, wherein:
the comparison path extends in such a manner through the container that in the case of presence of said accretion layer on the inner walls of the container a ratio of a sum of the lengths of two accretion segments of the comparison path, said accretion segments extending through the accretion layer, to the length of an additional segment of the comparison path extending between the two accretion segments of the comparison path is different from the ratio of the sum of the lengths of two accretion segments of the measuring path extending through the accretion layer to the length of the additional segment of the measuring path extending between the two accretion segments of the measurement path;
said comparison measuring system including a detector, wherein said detector measures a comparison gamma ray radiation intensity emerging from the container along the comparison path;
said comparison measuring system including an evaluation unit, wherein said evaluation unit, based on calibration data of the comparison measuring system ascertained in the case of accretion free container and the measured comparison gamma ray radiation intensity, determines a comparison measurement result corresponding to the measured variable, and provides said comparison measurement result for detection of accretion formation in the container, and
an evaluating unit connected to the measuring system and to the comparison measuring system, wherein said evaluating unit determines a deviation between the measurement result of the measuring system and the comparison measurement result of the comparison measuring system and detects accretion based on said deviation.

7. The radiometric measuring arrangement as claimed in claim 6, wherein:
said measuring system and said comparison measuring system each has a radioactive radiator arranged externally on the container and the detectors of said measuring system and said comparison measuring system are each arranged externally on the container on a side of the container lying opposite said respective radiator along the measuring path or, the comparison path, respectively.

8. The radiometric measuring arrangement as a claimed in claim 6, wherein:
there is provided arranged externally on the container only a single radioactive radiator, wherein said radiator transmits gamma ray radiation along said measuring path and along said comparison path;
said measuring path and said comparison path extend at an angle to one another;
said detector of said measuring system is arranged- externally on the container on a side of the container lying opposite said single radiator along said measuring path; and
said detector of said comparison measuring system is arranged externally on the container on a side of the container lying opposite said single radiator along said comparison path.

9. A radiometric measuring arrangement
for monitoring a fill level of a fill substance located in a tubular container exceeding or falling below a predetermined level in the container and for detecting accretion occurring in the form of an accretion layer deposited on the inner walls of said container, comprising:
a measuring system arranged at a height corresponding to said predetermined level,
wherein said measuring system sends gamma ray radiation along a measuring path through the container, said measuring system including a detector, wherein said detector measures a gamma ray radiation intensity emerging from the container along the measuring path,
wherein said measuring system includes an evaluation unit, wherein said evaluation unit, based on calibration data of the measuring system ascertained in case of the accretion free container and the measured gamma ray radiation intensity determines and outputs a measurement result corresponding to a measured variable corresponding to an average density of material present in the container along the measurement path,
wherein said measuring system monitors said fill level of said substance exceeding or falling below said predetermined fill level based on the measured radiation intensity or based on the measurement result, and
wherein said measuring system has an output, wherein said measuring system outputs the measurement result corresponding to the measured gamma ray radiation intensity and to the calibration data ascertained in the case of the accretion free container via said output of said measuring system,
a comparison measuring system,
wherein said comparison measuring system sends gamma ray radiation along a comparison path through the container, wherein:
the comparison path extends in such a manner through the container that, in the case of presence of said accretion layer on the inner walls of the container a ratio of a sum of the lengths of two accretion segments of the comparison path, said accretion segments extending through the accretion layer, to the length of an additional segment of the comparison path extending between the two accretion segments of the comparison path is different from the ratio of the sum of the lengths of two accretion segments of the measuring path extending through the accretion layer to the length of an additional segment of the measuring path extending between two accretion segments of the measurement path,
wherein said comparison measuring system includes a detector, wherein said detector measures a comparison gamma ray radiation intensity emerging from the container along the comparison path:

wherein said comparison measuring system includes an evaluation unit, wherein said evaluation unit, based on calibration data of the comparison measuring system ascertained in the case of accretion free container and the measured comparison gamma ray radiation intensity, determines a comparison measurement result corresponding a measured variable corresponding to an average density of material present in the container along the comparison path; and provides said comparison measurement result for detection of accretion formation in the container, and wherein said comparison measuring system has an output, wherein said comparison system outputs the comparison measurement result corresponding to the measured comparison gamma ray radiation intensity and to the calibration data ascertained in the case of the accretion free container via said output of said comparison system, and an evaluating unit connected to the measuring system and to the comparison measuring system, wherein said evaluating unit determines a deviation between the measurement result of the measuring system and the comparison measurement result of the comparison measuring system and detects accretion based on said deviation.

* * * * *